(12) United States Patent
Kim et al.

(10) Patent No.: US 11,919,156 B2
(45) Date of Patent: Mar. 5, 2024

(54) METHOD AND APPARATUS FOR RECOGNIZING USER MOTION

(71) Applicant: Samsung Electronics Co., Ltd., Suwon-si (KR)

(72) Inventors: Kyung-Rock Kim, Yongin-si (KR); Youngbo Shim, Seoul (KR); Sunghwan Ahn, Seoul (KR); Jusuk Lee, Hwaseong-si (KR); Bokman Lim, Yongin-si (KR); Jun-Won Jang, Seoul (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 640 days.

(21) Appl. No.: 17/070,895

(22) Filed: Oct. 14, 2020

(65) Prior Publication Data

US 2021/0022945 A1    Jan. 28, 2021

Related U.S. Application Data

(63) Continuation of application No. 14/686,323, filed on Apr. 14, 2015, now Pat. No. 10,835,442.

(30) Foreign Application Priority Data

Oct. 20, 2014   (KR) .................. 10-2014-0141512

(51) Int. Cl.
*B25J 9/00*        (2006.01)
*A61B 5/00*        (2006.01)
(Continued)

(52) U.S. Cl.
CPC ........... *B25J 9/0006* (2013.01); *A61B 5/1116* (2013.01); *A61B 5/1122* (2013.01);
(Continued)

(58) Field of Classification Search
CPC .... B25J 9/0006; A61H 3/00; A61H 2003/007; A61H 2201/165; A61H 2201/5069;
(Continued)

(56) References Cited

U.S. PATENT DOCUMENTS 7,880,552 B2    2/2011   Yasuhara et al.
2010/0256537 A1   10/2010   Menga
(Continued)

FOREIGN PATENT DOCUMENTS

JP    2010-017390 A    1/2010
JP    5189911 B2    4/2013
(Continued)

OTHER PUBLICATIONS

KR Office Action for corresponding Korean Patent Application No. 10-2014-0141512 dated Dec. 28, 2020 and English translation thereof.
(Continued)

*Primary Examiner* — Jerrah Edwards
*Assistant Examiner* — Aren Patel
(74) *Attorney, Agent, or Firm* — Harness, Dickey & Pierce, P.L.C.

(57) ABSTRACT

A method and apparatus for recognizing a motion of a user are provided. The apparatus may map each of right leg angle information and left leg angle information to context information by comparing each of the right leg angle information and left leg angle information to a comparison value and/or preset threshold, may generate a motion event corresponding to the context information based on a criterion, and may recognize the motion of the user based on the motion event and a previous motion of the user.

20 Claims, 6 Drawing Sheets

(51) Int. Cl.
  *A61B 5/11* (2006.01)
  *A61H 1/02* (2006.01)
  *A61H 3/00* (2006.01)
  *G01P 13/00* (2006.01)

(52) U.S. Cl.
  CPC .......... *A61B 5/1123* (2013.01); *A61B 5/6823* (2013.01); *A61B 5/6828* (2013.01); *A61B 5/7264* (2013.01); *A61H 1/0244* (2013.01); *A61H 3/00* (2013.01); *A61B 5/7207* (2013.01); *A61B 2562/0219* (2013.01); *A61H 2003/007* (2013.01); *A61H 2201/1215* (2013.01); *A61H 2201/165* (2013.01); *A61H 2201/5058* (2013.01); *A61H 2201/5069* (2013.01); *A61H 2201/5084* (2013.01); *A61H 2201/5097* (2013.01); *G01P 13/00* (2013.01)

(58) Field of Classification Search
  CPC .... A61H 2201/5084; A61H 2201/5097; A61H 1/0244; A61H 2201/1215; A61H 2201/5058; A61B 5/1116; A61B 5/1122; A61B 5/1123; A61B 5/6823; A61B 5/6828; A61B 5/7264; A61B 2562/0219; G01P 13/00
  See application file for complete search history.

(56) References Cited

U.S. PATENT DOCUMENTS

| | | |
|---|---|---|
| 2011/0178639 A1 | 7/2011 | Kwon et al. |
| 2012/0101415 A1 | 4/2012 | Goffer et al. |
| 2012/0310122 A1* | 12/2012 | Endo .................. A61H 3/00 601/35 |
| 2013/0138020 A1* | 5/2013 | Yasuhara ............ A61H 1/0244 601/35 |
| 2013/0218345 A1 | 8/2013 | Lee et al. |
| 2014/0142475 A1* | 5/2014 | Goldfarb .............. A61H 1/0262 601/35 |
| 2015/0182408 A1* | 7/2015 | Roh .................... B25J 9/0006 482/51 |

FOREIGN PATENT DOCUMENTS

| | | |
|---|---|---|
| KR | 10-2008-0046682 A | 5/2008 |
| KR | 10-2011-0076418 A | 7/2011 |
| KR | 10-2013-0063230 A | 6/2013 |
| KR | 10-2013-0095973 A | 8/2013 |

OTHER PUBLICATIONS

Wang, Letian, et al., "Actively Controlled Lateral Gait Assistance in a Lower Limb Exoskeleton." 2013 IEEE/RSJ International Conference on Intelligent Robots and Systems. IEEE, (2013) <URL: https://doi.org/10.1109/IROS.2013.6696467>.

Jacquelin Perry, "Gait Analysis: Normal and Pathological Function," (2nd edition). Journal of Sports Science and Medicine, New Jersey: SLACK. ISBN: 978-1556427664, Section I: Fundamentals. (2010).

Alberto Alvarez-Alvarez, Human Gait Modeling Using a Genetic Fuzzy Finite State Machine. IEEE Transactions on Fuzzy Systems, vol. 20, No. 2, pp. 205-223. (2012) <URL: <https://doi.org/10.1109/TFUZZ.2011.2171973>>.

* cited by examiner

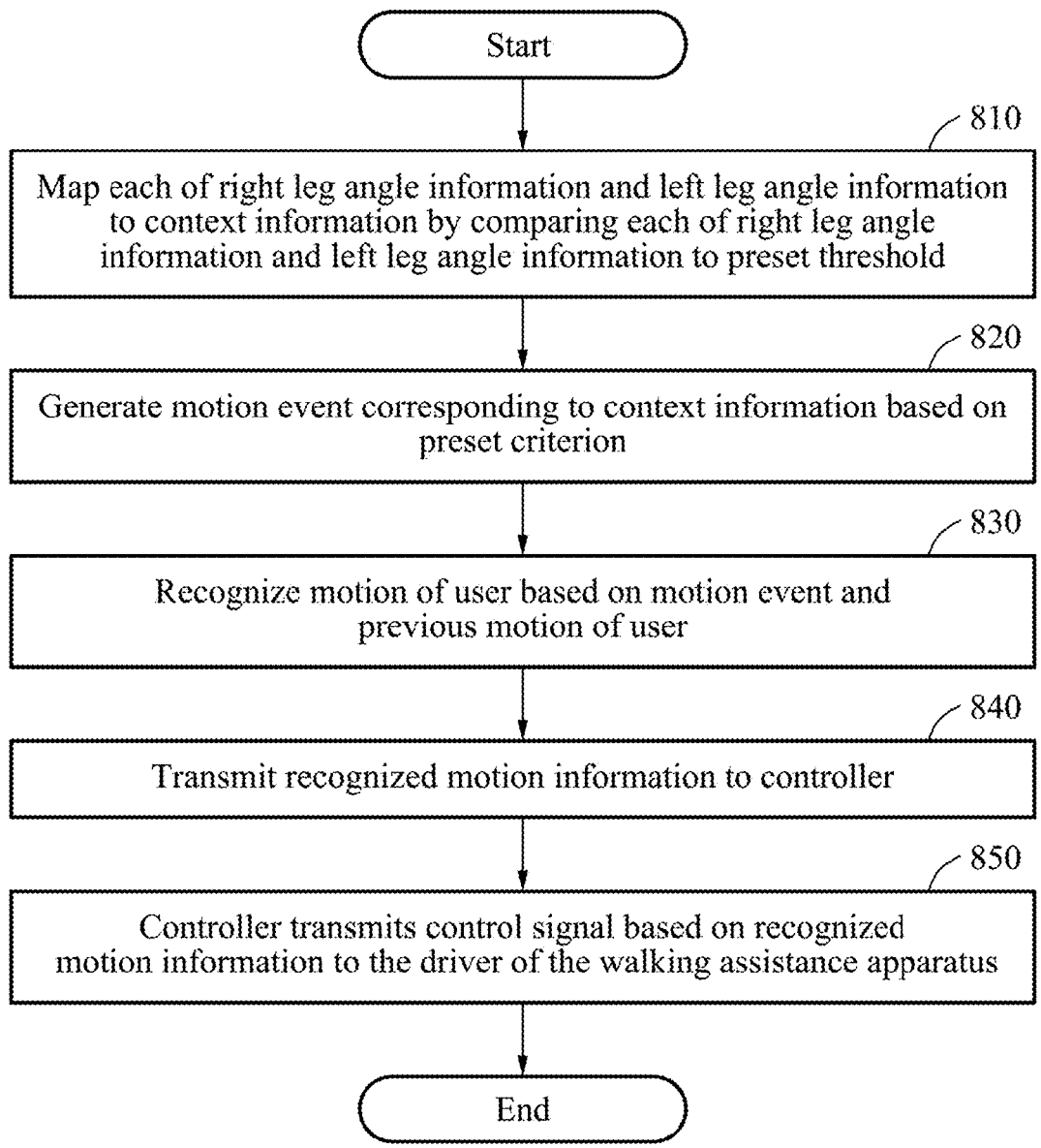

METHOD AND APPARATUS FOR RECOGNIZING USER MOTION

CROSS-REFERENCE TO RELATED APPLICATION

The present application is a continuation of and claims the benefit of priority under 35 U.S.C. § 120 to U.S. patent application Ser. No. 14/686,323, filed on Apr. 14, 2015, which claimed the benefit of priority of Korean Patent Application No. 10-2014-0141512, filed on Oct. 20, 2014, in the Korean Intellectual Property Office, the disclosures of each of which are incorporated herein by reference in their entireties.

BACKGROUND

1. Field

Some example embodiments relate to a method and apparatus for recognizing a motion of a user, and more particularly, to a method and apparatus for recognizing a motion of a user based on measured biometric data of a user.

2. Description of the Related Art

When a conventional motion assistance is provided to a user using a motion assistance apparatus regardless of the movements or motions of the user, effective motion assistance may not be provided. For example, conventional motion assistance apparatuses may only provide set motion assistance, and this may be the case regardless of the movements or motions of the user. Accordingly, it may be impossible to provide a motion assistance based on a characteristic of the user's motion.

SUMMARY

Some example embodiments relate to a method of recognizing a motion of a user.

A method may be provided to provide motion assistance suitable for each motion of a user using a motion assistance and/or walking assistance apparatus. Additionally, an improved and/or optimized motion assistance may be provided by avoiding unnecessary motion assistance for each motion of the user.

In some example embodiments, the method may include mapping each of right leg angle information and left leg angle information to context information according to a comparison of each of the right leg angle information and left leg angle information to a comparison value, generating a motion event corresponding to the context information based on a desired and/or preset criterion, and recognizing a motion of the user, based on the motion event and a previous motion of the user. Information based on the results of the recognized motion may be provided to a walking assistance apparatus to improve the assistance provided by the walking assistance apparatus to a user.

The right leg angle information and left leg angle information may be calculated, based on sensed and/or measured upper body angle information and sensed and/or measured right and left hip joint angle information.

The right leg angle information and left leg angle information may be calculated by performing a calculation on the upper body angle information from the right and left hip joint angle information.

The generating may include verifying a duration of the motion event based on the desired and/or preset criterion, and generating the motion event, when the duration is equal to or longer than a preset period of time and/or threshold time.

The motion event may include a swing event, an ascending event, a descending event, a flexion event, and an extension event. The motion of the user may include a standing motion, a walking motion, a sitting motion, a sit-to-stand motion, and a stand-to-sit motion.

The recognizing may include recognizing the motion, using a finite state machine (FSM) based on a relationship between motions of the user.

The FSM may include at least one state based on a motion of the user, and a transition condition between the at least one state may be based on the motion event.

Some example embodiments relate to an apparatus for recognizing a motion of a user.

In some example embodiments, the apparatus may include a mapping unit configured to map each of right leg angle information and left leg angle information to context information based on a comparison of the right leg angle information and left leg angle information to a comparison value, a motion event generator configured to generate a motion event corresponding to the context information based on a preset and/or desired criterion, and a motion recognizer unit configured to recognize a motion of the user based on the motion event and a previous motion of the user.

The right leg angle information and left leg angle information may be calculated based on sensed and/or measured upper body angle information and sensed and/or measured right and left hip joint angle information.

The right leg angle information and left leg angle information may be calculated by performing a calculation on the upper body angle information from the right and left hip joint angle information.

The motion event generator may be configured to verify a duration of the motion event based on the preset and/or desired criterion, and to generate the motion event when the duration is equal to or longer than a preset period of time and/or threshold time.

The motion recognizer may be configured to recognize the motion using a finite state machine (FSM) based on a relationship between motions of the user.

The FSM may include at least one state based on a motion of the user, and a transition condition between the at least one state may be based on the motion event.

Some example embodiments relate to a walking assistance apparatus.

In some example embodiments, the walking assistance apparatus may include a driver configured to drive a right hip joint and a left hip joint of a user, a sensor configured to sense and/or measure right and left hip joint angle information, an inertial measurement unit (IMU) sensor configured to sense and/or measure upper body angle information of the user, and a controller configured to map each of right leg angle information and left leg angle information to context information based on a comparison of each of the right leg angle information and left leg angle information to a comparison value, to generate a motion event corresponding to the context information based on a preset and/or desired criterion to recognize a motion of the user based on the motion event and a previous motion of the user, and to control the driver, the right leg angle information and left leg angle information being calculated based on the right and left hip joint angle information and the upper body angle information.

The controller may be configured to verify a duration of the motion event based on the preset and/or desired criterion and to generate the motion event when the duration is equal to or longer than a preset period of time and/or threshold time.

The controller may be configured to recognize the motion using an FSM based on a relationship between motions of the user.

Additional aspects of some example embodiments will be set forth in part in the description which follows and, in part, will be apparent from the description, or may be learned by practice of the disclosure.

BRIEF DESCRIPTION OF THE DRAWINGS

The foregoing and other features of some example embodiments will be apparent from the more particular description of non-limiting embodiments, as illustrated in the accompanying drawings in which like reference characters refer to like parts throughout the different views. The drawings are not necessarily to scale, emphasis instead being placed upon illustrating principles of some example embodiments. In the drawings:

FIG. 8 is a flowchart illustrating a method of recognizing a motion of a user according to some example embodiments.

DETAILED DESCRIPTION

Figure 1:
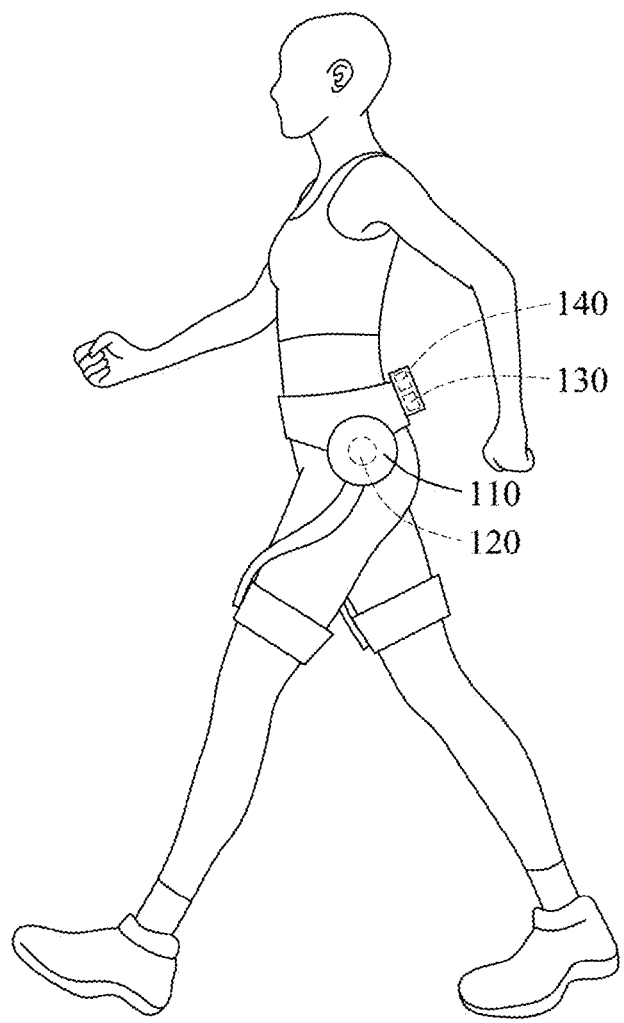
FIG. 1 illustrates a user wearing a walking assistance apparatus according to some example embodiments.

Hereinafter, some example embodiments will be described in detail with reference to the accompanying drawings. The scope of the right may, however, should not be construed as being limited to the example embodiments set forth herein. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of some example embodiments.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, terms used herein are selected from general terms being used in the related arts. Yet, the meanings of the terms used herein may be changed depending on a change and/or development of technologies, a custom, or preference of an operator in the art. Accordingly, the terms are merely examples to describe the example embodiments, and should not be construed as limited to the technical idea of the example embodiments.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

FIG. 1 illustrates a user wearing a walking assistance apparatus according to some example embodiments.

Referring to FIG. 1, the walking assistance apparatus may include a driver 110, a sensor 120, an inertial measurement unit (IMU) sensor 130, and a controller 140. FIG. 1 illustrates an example of a hip-type walking assistance apparatus, however, there is no limitation thereto. Accordingly, the walking assistance apparatus may be applicable to, for example, a walking assistance apparatus for supporting an entire pelvic limb, or a walking assistance apparatus for supporting a portion of a pelvic limb. Also, the walking assistance apparatus may be applicable to, for example, any type of walking assistance apparatus for assisting the walking of a user, for example, a walking assistance apparatus for supporting a portion of a pelvic limb, a walking assistance apparatus for supporting up to a knee, and a walking assistance apparatus for supporting up to an ankle. Furthermore, it is obvious to one of ordinary skill in the art that the walking assistance apparatus may be applicable to an apparatus for assisting the physical rehabilitation of a user.

Additionally, while the assistance apparatus is referred to as a walking assistance apparatus in accordance with discussion of some example embodiments, example embodiments presented herein are not limited thereto and may also be applied to other types or forms of physical assistance apparatuses, such as apparatuses designed to assistance a user's arm movements and/or functionality, or apparatuses designed to provide additional physical strength to a user's movements. Further, while some example embodiments are discussed in reference to use by a human being, one of ordinary skill in the art would appreciate that some example embodiments disclosed herein may also be applied to other beings and/or objects, such as animals, machines and/or robots, including surgical robots, assembly line/industrial robots, or autonomous robots.

The driver 110 may provide a user with motion assistance, and may be disposed on, for example, a right hip portion and a left hip portion of the user. The sensor 120 may measure hip joint angle information for both hip joints of the user while the user is moving. The sensor 120 may be disposed in the driver 110. The hip joint angle information measured by the sensor 120 may include, for example, at least one of the angles of either or both hip joint, a difference between the angles of either or both hip joints, and the direction of motion for either or both hip joint. In some of the example embodiments, the hip joint angle information may be referred to as "right and left hip joint angle information."

The IMU sensor 130 may measure the user's upper body angle information while the user is stationary or ambulatory. Right leg angle information and left leg angle information of the user may be calculated based on the upper body angle information measured by the IMU sensor 130 and the hip joint angle information measured by the sensor 120.

The controller 140 may map each of the right leg angle information and left leg angle information to context information by comparing each of the right leg angle information and left leg angle information to a comparison value and/or preset threshold, and may generate a motion event corresponding to the context information based on a preset and/or desired criterion. The controller 140 may recognize a motion of the user based on a previous motion of the user and the generated motion event. The controller 140 may also include a processor and memory for the processing of the information and data sensed and/or measured by the IMU sensor.

The controller 140 may recognize the motion of the user as described above, and may output a control signal to control the driver 110. Based on the control signal output from the controller 140, the driver 110 may provide the user with a motion assistance suitable for the recognized motion.

Figure 2:
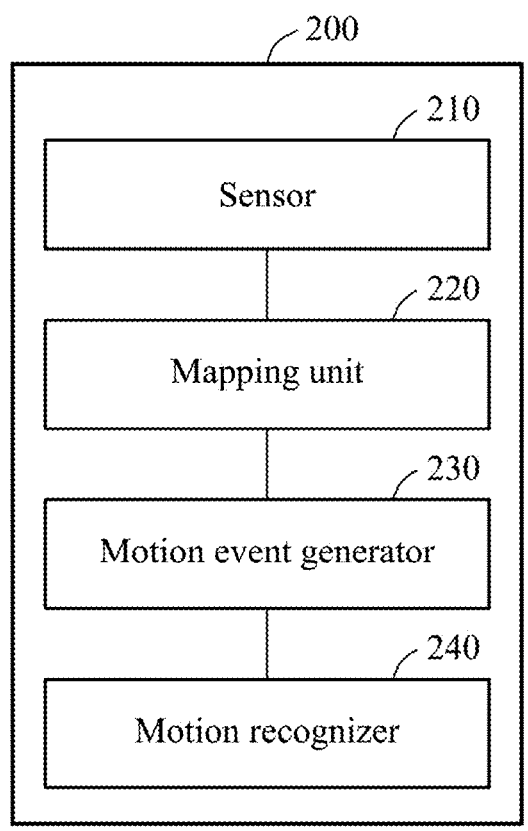
FIG. 2 is a block diagram illustrating a configuration of an apparatus for recognizing a motion of a user according to some example embodiments.

FIG. 2 is a block diagram illustrating a configuration of an apparatus 200 for recognizing a motion of a user according to some example embodiments.

Referring to FIG. 2, the apparatus 200 may include a sensor 210, a mapping unit 220, a motion event generator 230, and a motion recognizer 240.

The sensor 210 may sense and/or measure right and left hip joint angle information, and upper body angle information. For example, the sensor 210 may sense and/or measure, based on a direction of gravity, the right and left hip joint angle information, and the upper body angle information.

The sensor 210 may individually sense and/or measure the right and left hip joint angle information, and the upper body angle information. For example, the right and left hip joint angle information may be sensed and/or measured using an encoder, and the upper body angle information may be sensed and/or measured using an IMU sensor. The sensor 210 may include the encoder and the IMU sensor.

The mapping unit 220 may map each of right leg angle information and left leg angle information to context information by comparing each of the right leg angle information and left leg angle information to a comparison value and/or preset threshold. The right and left leg angle information may be calculated, based on the right and left hip joint angle information, and the upper body angle information.

The right and left leg angle information may be calculated based on the right and left hip joint angle information and the upper body angle information that are sensed and/or measured by the sensor 210, instead of being directly sensed and/or measured by the sensor 210. For example, the right and left leg angle information may be calculated by subtracting the upper body angle information from the right and left hip joint angle information.

As described above, the right and left leg angle information used to recognize a motion of the user may be calculated by the mapping unit 220 based on the right and left hip joint angle information and the upper body angle information.

For example, when the sensors necessary for sensing and/or measuring all of the data required to recognize a motion of a user is available and enabled in a walking assistance apparatus, a process of indirectly acquiring the required data based on other data, as described above, may not be necessary.

However, to sense and/or measure all of the required data, the configuration of the walking assistance apparatus may be complicated. In addition, data may not be sensed and/or measured due to the structure of the type of walking assistance apparatus. Accordingly, it may be difficult to recognize a motion of a user based solely on directly measured data.

Thus, when data required to recognize a motion of a user is acquired based on data capable of being sensed and/or measured, the configuration of the walking assistance apparatus may be simplified, and the data may be applied to recognize the motion of the user regardless of a type of the walking assistance apparatus.

The right and left leg angle information may include a right leg angle, a left leg angle, a right leg angular velocity, a left leg angular velocity, and a difference between the right leg angle and the left leg angle. Additionally, the right and left leg angle information may further include a right leg sit angle and a left leg sit angle to distinguish an extension event from a flexion event among motion events of the user. The extension event and the flexion event may correspond to a stop state. In some example embodiments, a leg sit angle may be defined as a leg angle measured in a sitting motion.

The mapping unit 220 may compare each of the right leg angle information and left leg angle information to the comparison value and/or preset threshold. The comparison value and/or threshold may be based on experimental data for a change in the right and left leg angle information based on each motion of the user.

The mapping unit 220 may compare each of the right leg angle information and left leg angle information to the comparison value and/or preset threshold, and may map each of the right leg angle information and left leg angle information to digitized context information. In an example, when the right leg angle information is less than a negative value of the threshold, the mapping unit 220 may map the right leg angle information to "−1." In another example, when the right leg angle information is greater than the comparison value and/or threshold, the mapping unit 220 may map the right leg angle information to "1." In still another example, when the right leg angle information is equal to or greater than the negative value of the comparison value and/or threshold, and is equal to or less than the comparison value and/or threshold, the mapping unit 220 may map the right leg angle information to "0."

As described above, the mapping unit 220 may map each of the right leg angle information and left leg angle information to the digitized context information, by comparing each of the right leg angle information and left leg angle information to the comparison value and/or threshold. The digitized context information may be used to generate a motion event. A process of mapping the right and left leg angle information to context information will be further described with reference to FIG. 3.

The motion event generator 230 may generate a motion event corresponding to the context information mapped in the mapping unit 220 based on a preset and/or desired criterion. The motion event may include but is not limited to, for example, a swing event—such as the swinging of a leg, an ascending event—such as the lifting of a leg, a descending event—such as the lowering of a leg, a flexion event—such as bending a leg, or an extension event—such as standing up with legs straight, etc.

The motion event may refer to a change in a motion of a leg of the user recognized based on information sensed and/or measured by the sensor 210 to recognize a current motion of the user. In other words, the current motion of the user may be recognized based on the motion event and a previous motion of the user, rather than the motion event being recognized as a final motion of the user.

In an example, when a swing event occurs in a standing motion, that is, the previous motion of the user, the current motion of the user may be recognized as a walking motion. In another example, when a swing event occurs in a sitting motion, that is, the previous motion, the current motion may also be recognized as a walking motion.

Motions of the user may be consecutively performed and accordingly, the current motion may be recognized differently based on the previous motion, despite an occurrence of the same motion event. The motion event may be, for example, a motion of a leg of the user used to recognize the current motion.

The motion event generator 230 may generate a motion event corresponding to the mapped context information based on the preset and/or desired criterion. The motion event generator 230 may determine whether a combination of the mapped context information corresponds to a desired and/or predetermined motion event based on the preset and/or desired criterion, and may generate a motion event corresponding to the combination of the context information.

The motion event generator 230 may verify a duration of the motion event. For example, when the duration is equal to or longer than a preset and/or given period of time, the motion event may be generated by the motion event generator.

By verifying the duration of the motion event, it is possible to filter out data noise sensed and/or measured by the sensor 210, or an unclear motion of the user, and thus it may possible to prevent a change in a motion from being unnecessarily and/or frequently sensed and/or measured by the apparatus. Thus, it is possible to achieve reliable results using the motion event generator.

A method by which the motion event generator 230 generates a motion event corresponding to a combination of context information based on a preset and/or desired criterion will be further described with reference to FIG. 5.

The motion recognizer 240 may recognize the motion of the user based on the motion event generated by the motion event generator 230 and the previous motion of the user. As described above, the current motion may be recognized differently based on the previous motion, despite the occurrence of the same motion event. Motions of the user may be consecutively performed and accordingly, the previous motion may need to be taken into consideration despite the occurrence of the same motion event.

The motion of the user may include but is not limited to, for example, a standing motion, a walking motion, a sitting motion, a sit-to-stand motion, or a stand-to-sit motion, etc. For instance, another motion of the user may be a jumping motion. To distinguish and recognize the above-described motions, the motion recognizer 240 may use a finite state machine (FSM) based on a relationship between motions of the user.

The FSM may include at least one state based on motions of the user. For example, each of the standing motion, the walking motion, the sitting motion, the sit-to-stand motion, and the stand-to-sit motion may each correspond to a single state.

Additionally, a transition condition between states of the FSM may be based on a motion event. Motions of the user may be consecutively performed as described above, and may transition to each other based on a desired and/or predetermined motion event. Accordingly, based on the above relationship between the motions, the transition condition may be set to be a motion event.

For example, when the previous motion is a standing motion, and when a swing event occurs, the current motion may be recognized as a walking motion. In this example, when a descending event occurs, the current motion may be recognized as a sitting state.

The motion recognizer 240 may recognize the motion of the user using the FSM. As described above, the FSM may include at least one state based on the motion of the user, and a transition condition between states of the FSM may be based on a motion event. A method by which the motion recognizer 240 recognizes the motion of the user using the FSM will be further described with reference to FIG. 6.

Thus, the apparatus 200 may recognize the motion of the user based on the sensed and/or measured right and left hip joint angle information and the sensed and/or measured upper body angle information. The apparatus 200 may then transmit the recognized motion data to a walking assistance apparatus, such as the walking assistance apparatus 100. By recognizing the current motion of the user, it is possible to provide improved and/or optimized motion assistance through the walking apparatus to the user based on the user's motion. The apparatus 200 may engage in bi-directional, or mono-directional, communications with a walking assistance apparatus, such as walking assistance apparatus 100. The communications may occur over a wired connection, such as via a bus interface, fiber optic connection, or Ethernet, etc. The apparatus 200 may also communicate with the walking assistance apparatus or a wireless connection, such as WiFi, Bluetooth, GSM, CDMA, LTE, RF, infrared, microwave, etc. Further, the apparatus 200 may be coupled to and/or integrated into a walking assistance apparatus. For example, the setting unit, recognition unit, and/or resampling unit may be integrated into various components of a walking assistance apparatus itself, such as the driver 100, the sensor 120, the IMU sensor 130, and/or the controller 140.

Figure 3:
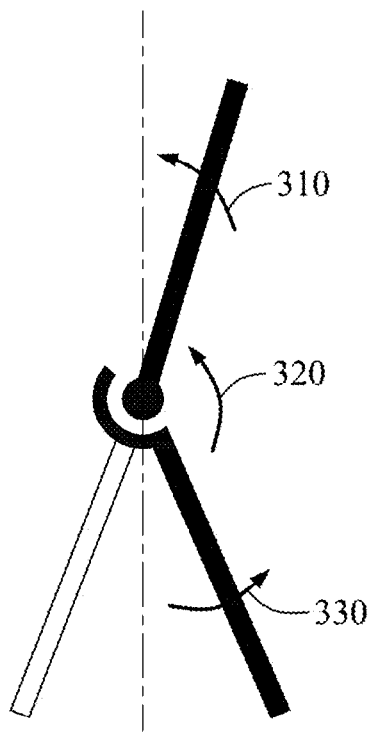
FIG. 3 illustrates a model obtained by simplifying a motion of a user according to some example embodiments.

FIG. 3 illustrates a model obtained by simplifying a motion of a user according to some example embodiments.

As shown in FIG. 3, an upper body and a lower body of the user are simplified based on a hip joint. A method of acquiring upper body angle information, right and left hip joint angle information, and right and left leg angle information of the user is described with reference to FIG. 3.

The sensor 210 of FIG. 2 may sense and/or measure upper body angle information 310 and right and left hip joint angle information 320 of the user based on the direction of gravity. For example, the right and left hip joint angle information 320 may be sensed and/or measured using an encoder, the upper body angle information 310 may be sensed and/or measured using an IMU sensor, and the sensor 210 may include the encoder and the IMU sensor.

The upper body angle information 310 may include an angle of an upper body and an angular velocity of the upper body. The right and left hip joint angle information 320 may include a right hip joint angle, a left hip joint angle, a right hip joint angular velocity, and a left hip joint angular velocity.

Right and left leg angle information 330 used to recognize a motion of the user may be calculated based on the upper body angle information 310 and the right and left hip joint angle information 320, instead of being directly sensed and/or measured by the sensor 210. For example, the right and left leg angle information 330 may be calculated by subtracting the upper body angle information 310 from the right and left hip joint angle information 320.

The right and left leg angle information 330 may include a right leg angle, a left leg angle, a right leg angular velocity, a left leg angular velocity, and a difference between the right leg angle and the left leg angle. Additionally, the right and left leg angle information 330 may further include a right leg sit angle and a left leg sit angle to recognize a motion of a user.

When it is difficult, inefficient and/or too expensive for a walking assistance apparatus to directly sense and/or measure the data that is used to recognize a user's motion as described above, the data may be derived, acquired and/or estimated based on the data that the walking assistance apparatus is capable of sensing and/or measuring.

Accordingly, a configuration of the walking assistance apparatus may also be simplified, and the walking assistance apparatus may be applied to recognize a user's motion regardless of a type of the walking assistance apparatus.

Right leg angle information and left leg angle information acquired by the above-described method may be compared to a comparison value and/or preset threshold, and may be mapped to digitized context information used to generate a motion event, by the mapping unit 220 of FIG. 2.

By comparing each of the right leg angle information and left leg angle information to the comparison value and/or preset threshold, each of the right leg angle information and left leg angle information may be mapped to digitized context information corresponding to each of the right leg angle information and left leg angle information, as shown in Table 1 below.

TABLE 1

|     | x    | e    | x < −e | −e ≤ x ≤ e | e < x |
|-----|------|------|--------|------------|-------|
| LA  | lq   | 5°   | −1     | 0          | 1     |
| RA  | rq   | 5°   | −1     | 0          | 1     |
| LSA | lq   | 45°  | −1     | 0          | 1     |
| RSA | rq   | 45°  | −1     | 0          | 1     |
| DA  | lq-rq| 15°  | −1     | 0          | 1     |
| LW  | lw   | 2°/s | −1     | 0          | 1     |
| RW  | rw   | 2°/s | −1     | 0          | 1     |

In Table 1, LA and RA denote context information corresponding to a left leg angle, and context information corresponding to a right leg angle, respectively. LSA and RSA denote context information corresponding to a left leg sit angle, and context information corresponding to a right leg sit angle, respectively. DA denotes context information corresponding to a difference between the left leg angle and the right leg angle. LW and RW denote context information corresponding to a left leg angular velocity, and context information corresponding to a right leg angular velocity, respectively.

Additionally, x refers to a variable corresponding to right and left leg angle information, and may be actually compared to a threshold. lq and rq denote the left leg angle, and the right leg angle, respectively, and lq−rq denotes the difference between the left leg angle and the right leg angle. lw and rw denote the left leg angular velocity and the right leg angular velocity, respectively.

The context information LA and LSA may have the same variable, that is, lq, and the context information RA and RSA may have the same variable, that is, rq, because the context information LSA and RSA are introduced to distinguish an extension event from a flexion event among motion events of the user, instead of being separately sensed and/or measured and calculated by the sensor 210. The extension event and the flexion event may correspond to a stop state.

Accordingly, the context information LSA and RSA may be used to distinguish motion events, by using the same variable for the context information LA and LSA and the same variable for the context information RA and RSA, and by setting different thresholds.

Furthermore, e denotes a comparison value and/or preset threshold corresponding to each of right leg angle information and left leg angle information. The comparison value and/or threshold may be set because data may be sensed and/or measured by the sensor 210 due to a small movement, even when a movement corresponding to a motion event is not intended by a user. Accordingly, to perform filtering of an unintended small movement, the comparison value and/or threshold may be set. However, the comparison value and/or threshold e of Table 1 is merely an example for understanding of description, and there is no limitation thereto. Accordingly, the comparison value and/or threshold e may be set suitably for a characteristic of a user.

The mapping unit 220 may compare each of right leg angle information and left leg angle information to a comparison value and/or preset threshold, and may map each of the right leg angle information and left leg angle information to context information. In an example, when the right leg angle information is less than a negative value of a comparison value and/or threshold, the right leg angle information may be mapped to "4." In another example, when the right leg angle information is greater than the comparison value and/or threshold, the right leg angle information may be mapped to "1." In still another example, when the right leg angle information is equal to or greater than the negative value of the comparison value and/or threshold, and is equal to or less than the comparison value and/or threshold, the right leg angle information may be mapped to "0."

In an example, when the variable lq corresponding to the left leg angle is greater than 5° that is set as a comparison value and/or threshold in advance, the context information LA may be mapped to "1." In another example, when the variable lq is less than −5°, that is, a negative value of the comparison value and/or threshold, the context information LA may be mapped to "4." In still another example, when the variable lq is equal to or greater than −5° and is equal to or less than 5°, the context information LA may be mapped to "0."

As described above, each of the right leg angle information and left leg angle information may be mapped to context information through a comparison between the comparison value and/or preset threshold and each of the right leg angle information and left leg angle information. The mapped context information may be used to generate a motion event.

Figure 4:
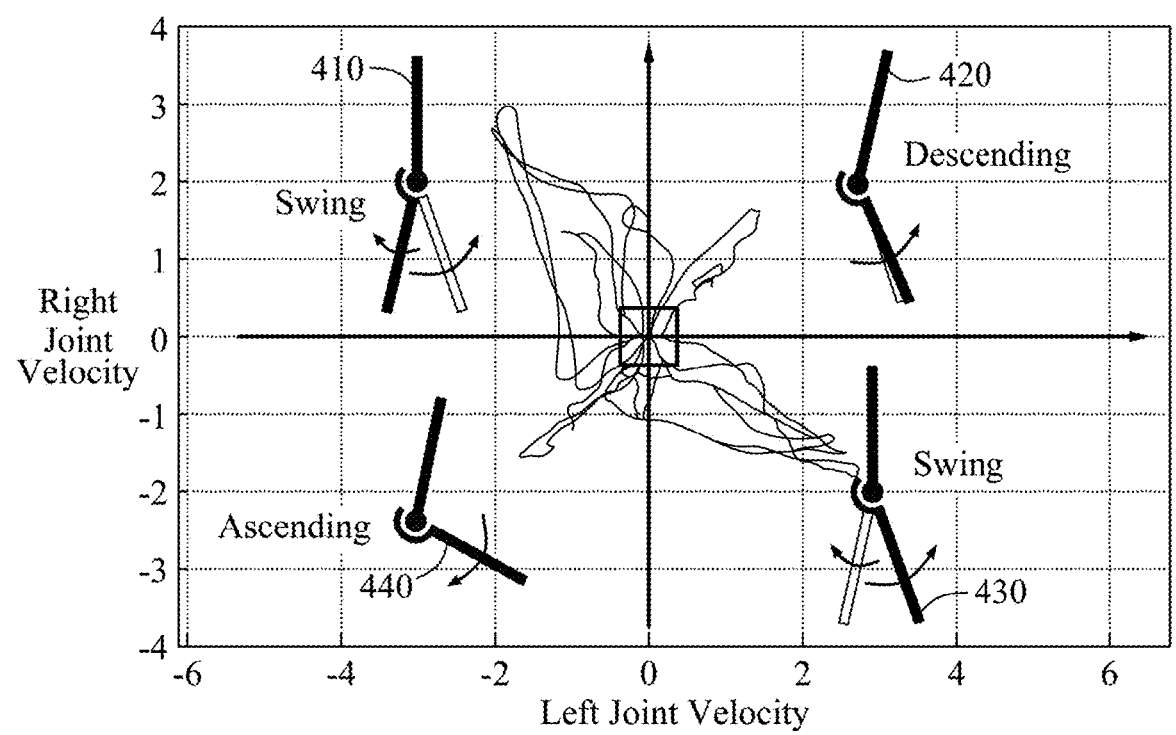
FIG. 4 is a graph illustrating motion events based on an angular velocity of each of a right leg and a left leg of a user according to some example embodiments.

FIG. 4 is a graph illustrating motion events based on an angular velocity of each of a right leg and a left leg of a user according to some example embodiments.

In the graph of FIG. 4, an x-axis represents a left leg angular velocity, and a y-axis represents a right leg angular velocity. Motion events of a user may correspond to quadrants of the graph, respectively.

In a second quadrant and a fourth quadrant of the graph, the right leg angular velocity and the left leg angular velocity have opposite signs, which may indicate that the right leg and the left leg may move in different directions. Accordingly, the second quadrant and the fourth quadrant may correspond to swing events 410 and 430, respectively.

In a first quadrant and a third quadrant of the graph, the right leg angular velocity and the left leg angular velocity have the same sign, which may indicate that the right leg and the left leg may move in the same direction.

In the first quadrant, both the right leg angular velocity and the left leg angular velocity have positive values, which may indicate that both the right leg and the left leg are moving in a flexion direction. A user's motion corresponding to movement of both the legs in the flexion direction may be, for example, a stand-to-sit motion, that is, a descending motion. Accordingly, the first quadrant may correspond to a descending event 420.

Conversely, in the third quadrant, both the right leg angular velocity and the left leg angular velocity have negative values, which may indicate that both the right leg and the left leg are moving in an extension direction. A user's motion corresponding to movement of both the legs in the extension direction may be, for example, a sit-to-stand motion, that is, an ascending motion. Accordingly, the third quadrant may correspond to an ascending event 440.

Thus, motion events may be based on characteristics of the right leg angular velocity and the left leg angular velocity. Additionally, a curve displayed in a central portion of the graph represents a relationship between the right leg angular velocity and the left leg angular velocity based on right and left leg angular velocity data of the user for each motion event, in the x-axis and the y-axis. Accordingly, a relationship between a right leg angular velocity and a left leg angular velocity calculated based on an actual user's motion may have the same characteristic as that of the relationship between the right leg angular velocity and the left leg angular velocity shown in the graph.

A method of actually distinguishing motion events based on a characteristic of right and left leg angle information and of generating a corresponding motion event will be described with reference to FIG. 5.

Figure 5:
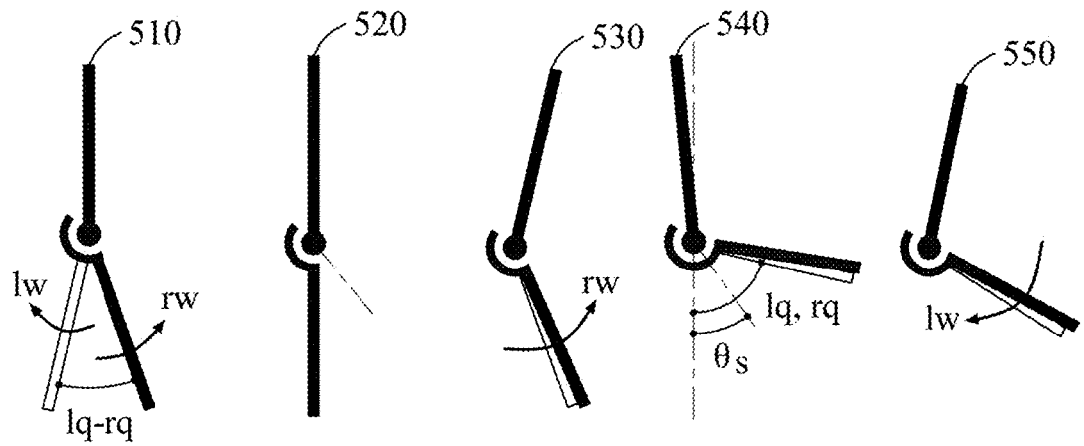
FIG. 5 illustrates models obtained by simplifying motion events according to some example embodiments.

FIG. 5 illustrates models obtained by simplifying motion events according to some example embodiments.

Referring to FIG. 5, motion events 510, 520, 530, 540, and 550 may include, for example, a swing event, an extension event, an ascending event, a flexion event, and a descending event. In addition to the swing events 410 and 430, the ascending event 440 and the descending event 420 of FIG. 4 based on a characteristic of leg angle information of a user, motion events may include an extension event and a flexion event that correspond to a stop state of the user. Table 2 shows a characteristic of right and left leg angle information for each motion event.

TABLE 2

| | Swing event | Extension event | Ascending event | Flexion event | Descending event |
|---|---|---|---|---|---|
| lq | · | $<\theta_s$ | · | $<\theta_s$ | · |
| rq | · | $<\theta_s$ | · | $<\theta_s$ | · |
| lq-rq | · | $\approx 0$ | $\approx 0$ | $\approx 0$ | $\approx 0$ |
| lw | +− | $\approx 0$ | − | $\approx 0$ | + |
| rw | −+ | $\approx 0$ | − | $\approx 0$ | + |
| duration | $>t_{swg}$ | $>t_{ext}$ | $>t_{asc}$ | $>t_{flx}$ | $>t_{dsc}$ |

The motion event 510 indicates a swing event. The swing event refers to an event in which legs cross, such as when a user is walking. In the swing event, a direction of a right leg angular velocity rw may be opposite to a direction of a left leg angular velocity lw. Accordingly, a motion event occurring when a right leg angular velocity and a left leg angular velocity have opposite signs may be determined as a swing event.

The motion event 520 indicates an extension event. In the extension event, each of the right leg angular velocity rw and the left leg angular velocity lw may have a value close to "0," and both a left leg and a right leg may be extended so that a left leg angle lq and a right leg angle rq may be equal to or less than a predetermined (or alternatively, given) angle $\theta_s$. Additionally, there is little difference lq−rq between both the legs.

The motion event 530 indicates an ascending event. In the ascending event, the right leg angular velocity rw and the left leg angular velocity lw may increase, that is, may be in a positive direction, and there is little difference lq−rq between both the legs.

The motion event 540 indicates a flexion event. In the flexion event, each of the right leg angular velocity rw and the left leg angular velocity lw may have a value close to "0," and both the left leg and the right leg may be bent so that the left leg angle lq and the right leg angle rq may be equal to or greater than the predetermined (or alternatively, given) angle $\theta_s$. Additionally, there is little difference lq−rq between both the legs.

The motion event 550 indicates a descending event. In the descending event, the right leg angular velocity rw and the left leg angular velocity lw may decrease, that is, may be in a negative direction, and there is little difference lq−rq between both the legs.

To generate each of the motion events, a condition based on each of the motion events may need to be maintained for longer than a duration set for each of the motion events. Accordingly, it is possible to filter out the data noise sensed and/or measured by the sensor 210, or an uncertain motion of the user, and it may be possible to prevent a false change in the user's motion from being unnecessarily, frequently sensed and/or measured. Thus, it is possible to acquire a reliable result.

Accordingly, the motion event generator 230 of FIG. 2 may verify a duration of a corresponding motion event. When the duration is equal to or longer than a preset and/or given period of time, the corresponding motion event may be finally generated.

Motion events may be based on right leg angle information and left leg angle information as described above, or may be simply distinguished as shown in Table 3, based on a combination of context information mapped by the mapping unit 220.

TABLE 3

| | LA | RA | LSA | RSA | DA | LW | RW | Duration |
|---|---|---|---|---|---|---|---|---|
| Descending event | 1 | 1 | • | • | 0 | −1 | −1 | >20 ms |
| Ascending event | 1 | 1 | • | • | 0 | 1 | 1 | >20 ms |
| Flexion event | • | • | −1 | −1 | 0 | 0 | 0 | >50 ms |
| Extension event | • | • | 1 | 1 | 0 | 0 | 0 | >50 ms |
| Swing event | • | • | • | • | • | 1 | −1 | >20 ms |
| | • | • | • | • | • | −1 | 1 | |

Table 3 shows conditions that context information corresponds to each of motion events, based on a characteristic of right and left leg angle information for each of the motion events. The motion event generator 230 may generate a motion event corresponding to context information mapped based on a preset and/or desired condition of Table 3. The generated motion event may be used to recognize a current motion of a user.

Figure 6:
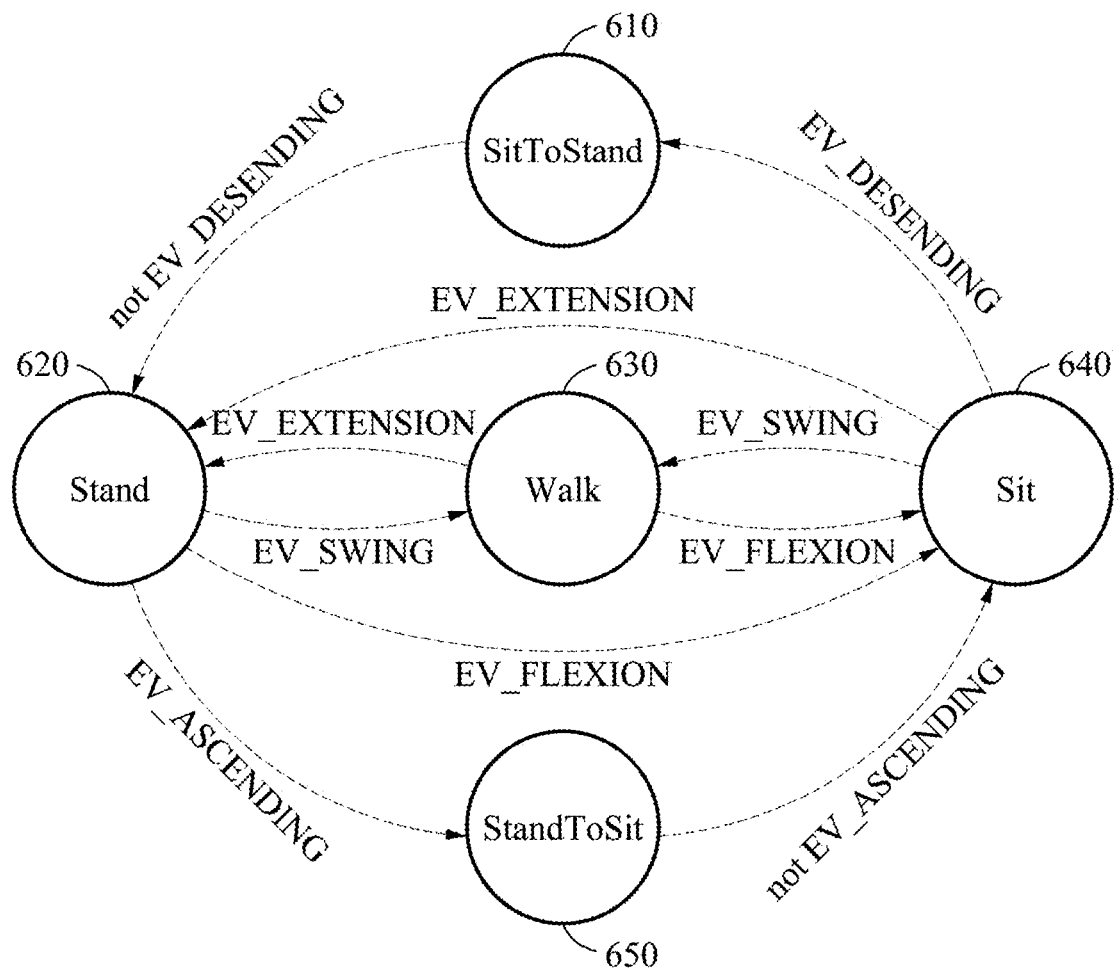
FIG. 6 illustrates a finite state machine (FSM) to recognize a motion of a user according to some example embodiments.

FIG. 6 illustrates an FSM to recognize a motion of a user according to some example embodiments.

The motion recognizer 240 of FIG. 2 may recognize a motion of a user, based on a previous motion of the user, and a motion event generated by the motion event generator 230 of FIG. 2. A current motion of the user may be recognized differently based on a previous motion of the user, despite an occurrence of the same motion event. Accordingly, the previous motion may need to be taken into consideration.

The motion of the user may include, for example, a standing motion, a walking motion, a sitting motion, a sit-to-stand motion, and a stand-to-sit motion. The motion recognizer 240 may use an FSM to distinguish and recognize the above motions. The FSM may be based on a relationship between motions of the user.

The FSM may include at least one state based on the motions of the user. Each of a sit-to-stand motion 610, a standing motion 620, a walking motion 630, a sitting motion 640, and a stand-to-sit motion 650 may correspond to a single state.

Additionally, a transition condition between states in the FSM may be based on a motion event. As described above, motions of the user may be consecutively performed, and may transition to each other based on a desired and/or predetermined motion event for each characteristic of the motions.

In an example, when a previous motion of a user corresponds to the sit-to-stand motion 610, and when one of motion events other than a descending event occurs, a current motion of the user may be recognized as the standing motion 620.

In another example, when the previous motion corresponds to the standing motion 620, and when a swing event is generated as a motion event, the current motion may be recognized as the walking motion 630. In this example, when a flexion event is generated as a motion event, the current motion may be recognized as the sitting motion 640. When an ascending event is generated, the current motion may be recognized as the stand-to-sit motion 650.

In still another example, when the previous motion corresponds to the walking motion 630, and when an extension event is generated as a motion event, the current motion may be recognized as the standing motion 620. In this example, when a flexion event is generated as a motion event, the current motion may be recognized as the sitting motion 640.

In yet another example, when the previous motion corresponds to the sitting motion 640, and when a descending event is generated as a motion event, the current motion may be recognized as the sit-to-stand motion 610. In this example, when an extension event occurs, the current motion may be recognized as the standing motion 620. When a swing event occurs, the current motion may be recognized as the walking motion 630.

In a further example, when the previous motion corresponds to the stand-to-sit motion 650, and when one of motion events other than an ascending event occurs, the current motion may be recognized as the sitting motion 640.

As described above, the motion recognizer 240 may recognize a current motion of a user, based on a previous motion of the user and a generated motion event. However, the FSM is merely an example for understanding of description, and there is no limitation thereto. Accordingly, it is obvious to one of ordinary skill in the art that different states and different transition conditions may be based on any other additional relationship between the motions of the user that the user and/or assistance apparatus is capable of.

Figure 7:
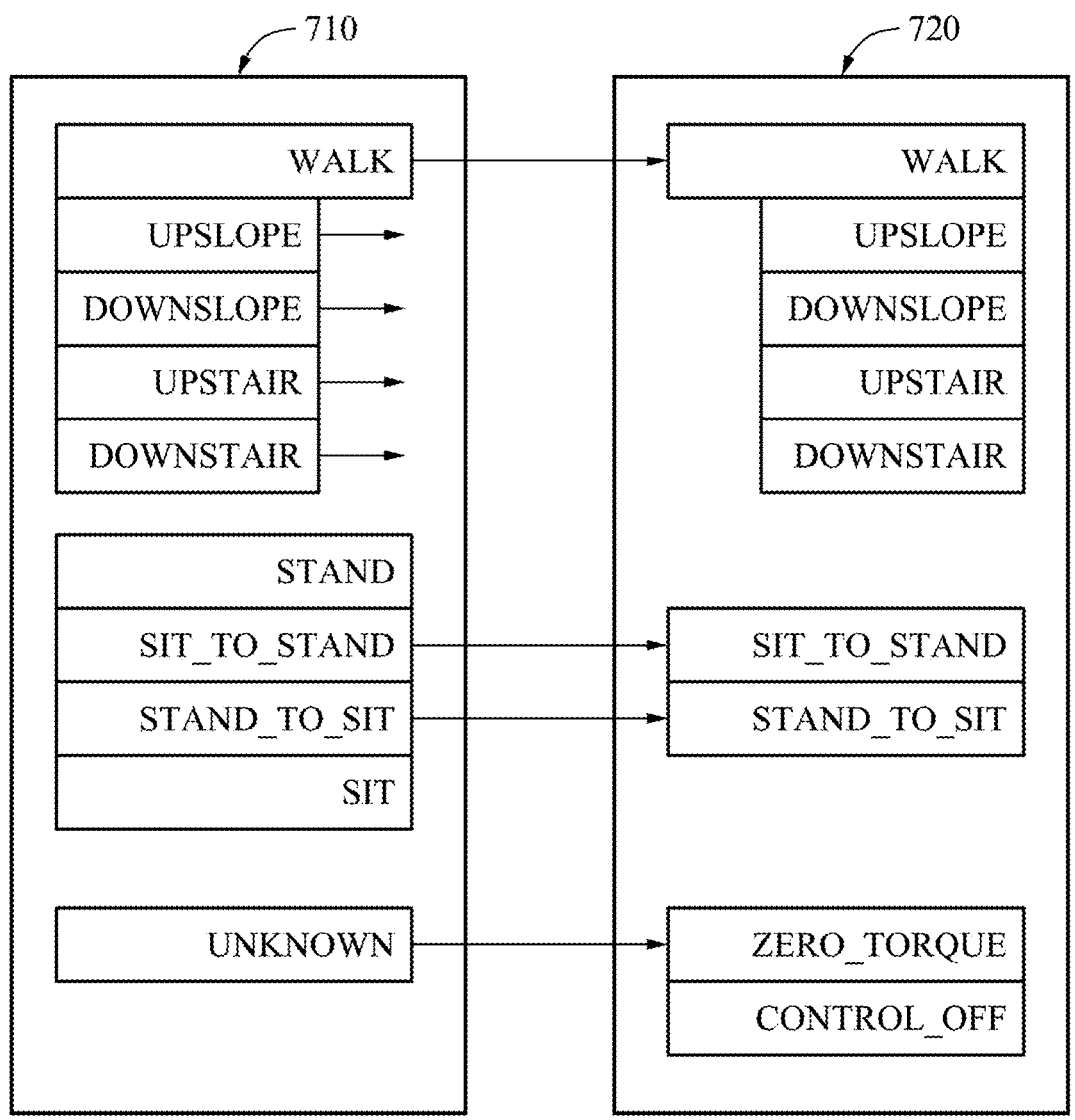
FIG. 7 is a block diagram illustrating a configuration of a walking assistance apparatus according to some example embodiments.

FIG. 7 is a block diagram illustrating a configuration of a walking assistance apparatus according to some example embodiments.

FIG. 7 illustrates a relationship between a controller 710 and a driver 720 included in a walking assistance apparatus, such as the walking assistance apparatus depicted in FIG. 1. The controller 710 may recognize a motion of a user. The driver 720 may provide the user with a motion assistance based on a control signal that is associated with the motion of the user and is generated by the controller 710.

The controller 710 may classify motions of the user as, for example but is not limited to, a walking motion, a standing motion, a sit-to-stand motion, a stand-to-sit motion, and a sitting motion, and may recognize each of the motions. When a motion of the user does not correspond to one of the recognized motions, the controller 710 may recognize and/or designate the motion as an unknown state, and it may control the driver 720 not to operate.

When a motion of the user is recognized as a walking motion, the controller 710 may divide the walking motion into walking in an upward inclined direction, walking in a downward inclined direction, walking up stairs, and walking down stairs, and may control the driver 720 to provide a walking assistance suitable for each walking motion. In FIG. 7, walking in an upward inclined direction, walking in a downward inclined direction, walking up stairs, and walking down stairs may be represented by "upslope," "downslope," "upstair," and "downstair," respectively.

The driver 720 may provide an assistance suitable for each motion of the user, in response to the control signal of the controller 710. In an example, when a motion of the user is recognized as a sit-to-stand motion and a stand-to-sit motion, the driver 720 may provide a motion assistance suitable for each of the sit-to-stand motion and the stand-to-sit motion.

In another example, when a motion of the user is recognized as a walking motion, the driver 720 may provide a motion assistance suitable for each of walking in the upward inclined direction, walking in the downward inclined direction, walking up stairs, and walking down stairs.

FIG. 8 is a flowchart illustrating a method of recognizing a motion of a user according to some example embodiments.

Referring to FIG. 8, in operation 810, the mapping unit 220 of FIG. 2 may map each of right leg angle information and left leg angle information to context information, by comparing each of the right leg angle information and left leg angle information to a comparison value and/or preset threshold. The right and left leg angle information may be calculated, based on right and left hip joint angle information and upper body angle information.

In an example, when the right leg angle information is less than a negative value of the threshold, the mapping unit 220 may map the right leg angle information to "4." In another example, when the right leg angle information is greater than the threshold, the mapping unit 220 may map the right leg angle information to "1." In still another example, when the right leg angle information is equal to or greater than the negative value of the threshold, and is equal to or less than the threshold, the mapping unit 220 may map the right leg angle information to "0."

Accordingly, the mapping unit 220 may compare each of the right leg angle information and left leg angle information to the threshold, and may map each of the right leg angle information and left leg angle information to digitized context information used to generate a motion event.

In operation 820, the motion event generator 230 of FIG. 2 may generate a motion event corresponding to the mapped context information, based on a preset and/or desired criterion. The motion event generator 230 may determine whether a combination of the mapped context information corresponds to a desired and/or predetermined motion event based on the preset and/or desired criterion, and may generate a motion event corresponding to the combination of the context information.

The motion event generator 230 may verify a duration of a corresponding motion event. When the duration is equal to or longer than a preset and/or given period of time, the corresponding motion event may be finally generated.

In operation 830, the motion recognizer 240 of FIG. 2 may recognize a motion of the user, based on the motion event generated by the motion event generator 230 and a previous motion of the user. The current motion may be recognized differently based on the previous motion, despite an occurrence of the same motion event. Motions of the user may be consecutively performed and accordingly, the previous motion may need to be taken into consideration, despite the occurrence of the same motion event.

The motion recognizer 240 may use an FSM based on a relationship between motions of the user to distinguish and recognize motions of the user. The FSM may include at least one state based on the motions of the user. For example, each of the standing motion, the walking motion, the sitting motion, the sit-to-stand motion, and the stand-to-sit motion may each correspond to a single state.

Additionally, a transition condition between states of the FSM may be based on a motion event. As described above, motions of the user may be consecutively performed, and may transition to each other based on a desired and/or predetermined motion event. Accordingly, based on the above relationship between the motions, the transition condition may be set to be a motion event.

In operation 840, the motion event generator 230 may transmit the recognized motion information to the controller 140 of FIG. 1.

In operation 850, the controller 140 may transmit control signals based on the recognized motion information to the driver 110 of FIG. 1 in order to provide improved and/or optimized motion assistance through the walking apparatus to the user based on the user's recognized motion.

As described above, by the method of FIG. 8, the motion of the user may be recognized based on sensed and/or measured right and left hip joint angle information and sensed and/or measured upper body angle information. Thus, it is possible to provide an optimized motion assistance based on the motion, by recognizing the motion of the user.

The units and/or modules described herein may be implemented using hardware components, software components, or a combination thereof. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of recognizing a motion of a user wearing a physical assistance apparatus, the method comprising:
    determining, using at least one processor, a right leg angle information of a right leg of the user and a left leg angle information of the left leg of the user based on sensing information obtained from a sensor of the physical assistance apparatus;
    determining, using the at least one processor, a motion event performed by the user based on the right leg angle information and the left leg angle information;
    recognizing, using the at least one processor, a current motion performed by the user the user based on the motion event and a previous motion performed by the user the user;
    controlling, using the at least one processor, a driver of the physical assistance apparatus to provide motion assistance to the user based on the recognized current motion; and
    the determining of the motion event including,
        determining the motion event as an ascending event or a descending event based on a moving direction of the right leg and a moving direction of the left leg, and
    the recognizing of the current motion including,
        recognizing the current motion as a stand-to-sit motion or a sit-to-stand motion based on whether the previous motion corresponds to a standing motion or a sitting motion, and whether the motion event is determined as the ascending event or the descending event.

2. The method of claim 1, wherein
the right leg angle information comprises information on a right leg angular velocity, and the left leg angle information comprises information on a left leg angular velocity; and
the determining of the motion event comprises,
    determining the motion event as the ascending event in response to a direction of the right leg angular velocity and a direction of the left leg angular velocity both increasing in a positive direction.

3. The method of claim 1, wherein
the right leg angle information comprises information on a right leg angular velocity, and the left leg angle information comprises information on a left leg angular velocity; and
the determining of the motion event comprises,
    determining the motion event as the descending event in response to a direction of the right leg angular velocity and a direction of the left leg angular velocity both decreasing a negative direction.

4. The method of claim 1, wherein the recognizing of the current motion comprises:
    recognizing the current motion as the standing motion in response to the previous motion performed by the user corresponding to the sit-to-stand motion and a motion event other than the descending event occurring; and
    recognizing the current motion as the sitting motion in response to the previous motion performed by the user corresponding to the stand-to-sit motion and a motion event other than the ascending event occuring.

5. The method of claim 1, wherein the determining of the motion event further comprises:
    determining the motion event as a swing event based on whether the moving direction of the right leg is opposite the moving direction of the left leg.

6. The method of claim 1, wherein
the right leg angle information comprises information on a right leg angular velocity and an angle of the right leg, and the left leg angle information comprises information on a left leg angular velocity and an angle of the left leg; and
the determining of the motion event further comprises,
    determining the motion event as an extension event based on the right leg angular velocity and the left leg angular velocity, and based on the right leg angle and the left leg angle.

7. The method of claim 6, wherein the determining of the motion event further comprises:
    determining the motion event as the extension event based on each of the right leg angular velocity and the left leg angular velocity being close to zero, and based on each of the right leg angle and the left leg angle being equal to or less than a desired value.

8. The method of claim 1, wherein
the right leg angle information comprises information on a right leg angular velocity and an angle of the right leg, and the left leg angle information comprises information on a left leg angular velocity and an angle of the left leg; and
the determining of the motion event further comprises,
    determining the motion event as a flexion event based on the right leg angular velocity and the left leg angular velocity, and based on the right leg angle and the left leg angle.

9. The method of claim 8, wherein the determining of the motion event further comprises:
    determining the motion event as the flexion event based on each of the right leg angular velocity and the left leg angular velocity being close to zero and the right leg angle and the left leg angle being greater than a desired value.

10. The method of claim 1, further comprising:
    determining, using the at least one processor, whether a duration of the motion event is equal to or greater than a desired period of time; and
    wherein the controlling the driver of the physical assistance apparatus further includes, controlling the driver of the physical assistance apparatus to provide the motion assistance based on the recognized current motion and results of the determining.

11. A physical assistance apparatus comprising:
    at least one sensor configured to sense information of the physical assistance apparatus;
    at least one driver configured to provide motion assistance to a user;
    memory having computer readable instructions stored thereon; and
    at least one processor configured to execute the computer readable instructions to, determine a right leg angle information of a right leg of the user and a left leg angle information of the left leg of the user based on the sensing information obtained from the at least one sensor;

determine a motion event performed by the user based on the right leg angle information and the left leg angle information;

recognize a current motion performed by the user based on the motion event and a previous motion performed by the user;

control the driver of the physical assistance apparatus to provide the motion assistance to the user based on the recognized current motion; and the determining of the motion event including,
 determining the motion event as an ascending event or a descending event based on a moving direction of the right leg and a moving direction of the left leg, and the recognizing of the current motion including,
 recognizing the current motion as a stand-to-sit motion or a sit-to-stand motion based on whether the previous motion corresponds to a standing motion or a sitting motion, and whether the motion event is determined as the ascending event or the descending event.

12. The physical assistance apparatus of claim 11, wherein
the right leg angle information comprises information on a right leg angular velocity, and the left leg angle information comprises information on a left leg angular velocity; and
the at least one processor is further caused to determine the motion event by,
 determining the motion event as the ascending event in response to a direction of the right leg angular velocity and a direction of the left leg angular velocity both increasing in a positive direction.

13. The physical assistance apparatus of claim 11, wherein
the right leg angle information comprises information on a right leg angular velocity, and the left leg angle information comprises information on a left leg angular velocity; and
the at least one processor is further caused to determine the motion event by,
 determining the motion event as the descending event in response to a direction of the right leg angular velocity and a direction of the left leg angular velocity both decreasing in a negative direction.

14. The physical assistance apparatus of claim 11, wherein the at least one processor is further caused to recognize the current motion by:
recognizing the current motion as the standing motion in response to the previous motion performed by the user corresponding to the sit-to-stand motion and a motion event other than the descending event occurring; and
recognizing the current motion as the sitting motion in response to the previous motion performed by the user corresponding to the stand-to-sit motion and a motion event other than the ascending event occurring.

15. The physical assistance apparatus of claim 11, wherein the at least one processor is further caused to determine the motion event by:
determining the motion event as a swing event based on whether the moving direction of the right leg is opposite the moving direction of the left leg.

16. The physical assistance apparatus of claim 11, wherein the right leg angle information comprises information on a right leg angular velocity and an angle of the right leg, and the left leg angle information comprises information on a left leg angular velocity and an angle of the left leg; and
the at least one processor is further caused to determine the motion event by,
 determining the motion event as an extension event based on the right leg angular velocity and the left leg angular velocity, and based on the right leg angle and the left leg angle.

17. The physical assistance apparatus of claim 16, wherein the at least one processor is further caused to determine the motion event by:
determining the motion event as the extension event based on each of the right leg angular velocity and the left leg angular velocity being close to zero, and based on each of the right leg angle and the left leg angle being equal to or less than a desired value.

18. The physical assistance apparatus of claim 11, wherein
the right leg angle information comprises information on a right leg angular velocity and an angle of the right leg, and the left leg angle information comprises information on a left leg angular velocity and an angle of the left leg; and
the at least one processor is further caused to determine the motion event by,
 determining the motion event as a flexion event based on the right leg angular velocity and the left leg angular velocity, and based on the right leg angle and the left leg angle.

19. The physical assistance apparatus of claim 18, wherein the at least one processor is further caused to determine the motion event by:
determining the motion event as the flexion event based on each of the right leg angular velocity and the left leg angular velocity being close to zero and the right leg angle and the left leg angle being greater than a desired value.

20. The physical assistance apparatus of claim 11, wherein the at least one processor is further caused to:
determine whether a duration of the motion event is equal to or greater than a desired period of time; and
wherein the controlling the driver of the physical assistance apparatus further includes, controlling the driver of the physical assistance apparatus to provide the motion assistance based on the recognized current motion and results of the determining.

* * * * *